(12) United States Patent
Peter et al.

(10) Patent No.: US 6,696,547 B2
(45) Date of Patent: Feb. 24, 2004

(54) MUTANT DEDD PROTEINS FOR REGULATING APOPTOSIS

(75) Inventors: Marcus Peter, Heidelberg (DE); Peter Krammer, Heidelberg (DE)

(73) Assignee: Deutsches Krebsforschungszentrum Stiftung des Offentlichen Rechts, Heidelberg (DE)

(*) Notice: Subject to any disclaimer, the term of this patent is extended or adjusted under 35 U.S.C. 154(b) by 0 days.

(21) Appl. No.: 09/733,167

(22) Filed: Dec. 8, 2000

(65) Prior Publication Data

US 2002/0099009 A1 Jul. 25, 2002

Related U.S. Application Data

(63) Continuation-in-part of application No. PCT/DE99/01712, filed on Jun. 8, 1999.

(30) Foreign Application Priority Data

Jun. 8, 1998 (DE) ............................. 198 25 621

(51) Int. Cl.[7] .................. A61K 38/17; C12N 14/435
(52) U.S. Cl. ........................ 530/358; 514/12
(58) Field of Search ................ 530/350, 358; 514/2, 12; 424/423, 484

(56) References Cited

U.S. PATENT DOCUMENTS

| | | | | |
|---|---|---|---|---|
| 4,925,677 A | * | 5/1990 | Feijen | 424/423 |
| 6,037,461 A | | 3/2000 | Alnemri | 536/23.5 |
| 6,207,801 B1 | * | 3/2001 | Alnemri | 530/350 |

FOREIGN PATENT DOCUMENTS

WO   WO 98/52963   11/1998

OTHER PUBLICATIONS

Berg et al (Mar. 5, 1999, Cancer Research 59, 1180–1183).*
Kastin, AJ, 2001, Life Science, 69(11):1305–12.*
Frost, SJ, 1993, J Cell Biochem, 52(2):227–36.*
Selbo et al (2002, Tumor Biol 23, 103–12, abstract only).*
Wang, J., Chen, R.,. and Julin, D. 2000 J. Biol. Chem. 275 (1): 507–513.*
Zhao, Z, "A novel gene from human dendritic cell," Dept. of Immunology, May 12, 1998.
Inohara, et al.,"CLARP, a death effector domain0containing protein interacts with caspase–8 and regulates apoptosis," Proc. Natl. Acad. Sci., Sep. 1997, 10717–10722.
Irmler, et al., "Inhibition of death receptor signals by cellular FLIP," Nature, vol. 388, Jul. 10, 1997, 190–195.
Stegh, et al., "DEDD, a novel death effector domain–containing protein, targeted to the nucleolus," The EMBO Journal, vol. 17, No. 20, pp. 5974–5986, 1998.
Leo, et al., "DEFT of novel death effector domain–containing molecule predominantly expressed in testicular germ cells,"Endocrinology, vol. 139 No. 12, pp. 4839–4848, Mar. 26, 1998.
Pan, "A novel molecule with a DED–like domain," Endocrinology, Aug. 10, 1998.

* cited by examiner

Primary Examiner—Mary E. Mosher
Assistant Examiner—Misook Yu
(74) Attorney, Agent, or Firm—Marianne Fuierer; Steven Hultquist; Mimi Yang (57) ABSTRACT

The invention relates to a protein for regulating apoptosis and to a nucleic acid encoding the protein. The protein and nucleic acids are useful in the regulation of apoptosis, and in methods for diagnosing or detecting apoptosis. The invention also relates to antibodies directed against the protein.

3 Claims, 8 Drawing Sheets

SEQUENCE LISTING

<160> NUMBER OF SEQ ID NOS: 10

<210> SEQ ID NO 1
<211> LENGTH: 318
<212> TYPE: PRT
<213> ORGANISM: Homo sapiens

<400> SEQUENCE: 1

```
Met Ala Gly Leu Lys Arg Arg Ala Ser Gln Val Trp Pro Glu Glu His
 1               5                  10                  15

Gly Glu Gln Glu His Gly Leu Tyr Ser Leu His Arg Met Phe Asp Ile
            20                  25                  30

Val Gly Thr His Leu Thr His Arg Asp Val Arg Val Leu Ser Phe Leu
        35                  40                  45
```

Phe Val Asp Val Ile Asp Asp His Glu Arg Gly Leu Ile Arg Asn Gly
 50                  55                  60

Arg Asp Phe Leu Leu Ala Leu Glu Arg Gln Gly Arg Cys Asp Glu Ser
 65                  70                  75                  80

Asn Phe Arg Gln Val Leu Gln Leu Leu Arg Ile Ile Thr Arg His Asp
                 85                  90                  95

Leu Leu Pro Tyr Val Thr Leu Lys Arg Arg Ala Val Cys Pro Asp
                100                 105                 110

Leu Val Asp Lys Tyr Leu Glu Glu Thr Ser Ile Arg Tyr Val Thr Pro
                115                 120                 125

Arg Ala Leu Ser Asp Pro Glu Pro Arg Pro Pro Gln Pro Ser Lys Thr
130                 135                 140

Val Pro Pro His Tyr Pro Val Val Cys Cys Pro Thr Ser Gly Pro Gln
145                 150                 155                 160

Met Cys Ser Lys Arg Pro Ala Arg Gly Arg Ala Thr Leu Gly Ser Gln
                165                 170                 175

Arg Lys Arg Arg Lys Ser Val Thr Pro Asp Pro Lys Glu Lys Gln Thr
                180                 185                 190

Cys Asp Ile Arg Leu Arg Val Arg Ala Glu Tyr Cys Gln His Glu Thr
                195                 200                 205

Ala Leu Gln Gly Asn Val Phe Ser Asn Lys Gln Asp Pro Leu Glu Arg
                210                 215                 220

Gln Phe Glu Arg Phe Asn Gln Ala Asn Thr Ile Leu Lys Ser Arg Asp
225                 230                 235                 240

Leu Gly Ser Ile Ile Cys Asp Ile Lys Phe Ser Glu Leu Thr Tyr Leu
                245                 250                 255

Asp Ala Phe Trp Arg Asp Tyr Ile Asn Gly Ser Leu Leu Glu Ala Leu
                260                 265                 270

Lys Gly Val Phe Ile Thr Asp Ser Leu Lys Gln Ala Val Gly His Glu
                275                 280                 285

Ala Ile Lys Leu Leu Val Asn Val Asp Glu Glu Asp Tyr Glu Leu Gly
290                 295                 300

Arg Gln Lys Leu Leu Arg Asn Leu Met Leu Gln Ala Leu Pro
305                 310                 315

<210> SEQ ID NO 2
<211> LENGTH: 1142
<212> TYPE: DNA
<213> ORGANISM: Homo sapiens
<220> FEATURE:
<221> NAME/KEY: misc_feature
<222> LOCATION: (1042)..(1042)
<223> OTHER INFORMATION: n represents any one of a, c, t, and g.
<220> FEATURE:
<221> NAME/KEY: misc_feature
<222> LOCATION: (1043)..(1043)
<223> OTHER INFORMATION: n represents any one of a, c, t, and g.
<220> FEATURE:
<221> NAME/KEY: misc_feature
<222> LOCATION: (1114)..(1114)
<223> OTHER INFORMATION: n represents any one of a, c, t, and g.

<400> SEQUENCE: 2
aaagcattgc gtacctgagc ccccagcatg gcgggcctaa agcggcgggc aagccaggtg      60
tggccagaag agcatggtga gcaggaacac gggctgtaca gcctgcaccg catgtttgac     120
atcgtgggca ctcatctgac acacagagat gtgcgcgtgc tttctttcct ctttgttgat     180
gtcattgatg accacgagcg tggactcatc cgaaatggac gtgacttctt attggcactg     240

-continued

```
gagcgccagg gccgctgtga tgaaagtaac tttcgccagg tgctgcagct gctgcgcatc    300
atcactcgcc acgacctgct gccctacgtc accctcaaga ggagacgggc tgtgtgccct    360
gatcttgtag acaagtatct ggaggagaca tcaattcgct atgtgacccc cagagccctc    420
agtgatccag aaccaaggcc tccccagccc tctaaaacag tgcctcccca ctatcctgtg    480
gtgtgttgcc ccacttcggg tcctcagatg tgtagcaagc ggccagcccg agggagagcc    540
acacttggga gccagcgaaa acgccggaag tcagtgacac cagatcccaa ggagaagcag    600
acatgtgaca tcagactgcg ggttcgggct gaatactgcc agcatgagac tgctctgcag    660
ggcaatgtct tctctaacaa gcaggaccca cttgagcgcc agtttgagcg ctttaaccag    720
gccaacacca tcctcaagtc ccgggacctg ggctccatca tctgtgacat caagttctct    780
gagctcacct acctcgatgc attctggcgt gactacatca atggctcttt attagaggca    840
cttaaaggtg tcttcatcac agactccctc aagcaagctg tgggccatga agccatcaag    900
ctgctggtaa atgtagacga ggaggactat gagctgggcc gacagaaact cctgaggaac    960
ttgatgctgc aagcattgcc ctgacctatt ccctcttctc actttgggga ctgttcccat   1020
cacccacctc tggagcttac annctgttct ggggtttgtt ctctacccct ccaaccaatc   1080
acacccctgg cctttttttt tttttttttt aaangaaaaa gacaaaagaa agtggaagtg   1140
gt                                                                   1142
```

<210> SEQ ID NO 3
<211> LENGTH: 318
<212> TYPE: PRT
<213> ORGANISM: Mus musculus

<400> SEQUENCE: 3

```
Met Ala Gly Leu Lys Arg Arg Ala Ser Gln Val Trp Pro Glu Glu Arg
1               5                   10                  15

Gly Glu Gln Glu His Gly Leu Tyr Ser Leu His Arg Met Phe Asp Ile
            20                  25                  30

Val Gly Thr His Leu Thr His Arg Asp Val Arg Val Leu Ser Phe Leu
        35                  40                  45

Phe Val Asp Val Ile Asp Asp His Glu Arg Gly Leu Ile Arg Asn Gly
    50                  55                  60

Arg Asp Phe Leu Leu Ala Leu Glu Arg Gln Gly Arg Cys Asp Glu Ser
65                  70                  75                  80

Asn Phe Arg Gln Val Leu Gln Leu Leu Arg Ile Ile Thr Arg His Asp
                85                  90                  95

Leu Leu Pro Tyr Val Thr Leu Lys Lys Arg Arg Ala Val Cys Pro Asp
            100                 105                 110

Leu Val Asp Lys Tyr Leu Glu Glu Thr Ser Ile Arg Tyr Val Thr Pro
        115                 120                 125

Arg Ala Leu Ser Asp Pro Glu Pro Arg Pro Pro Gln Pro Ser Lys Thr
    130                 135                 140

Val Pro Pro His Tyr Pro Val Cys Cys Pro Thr Ser Gly Ser Gln
145                 150                 155                 160

Met Cys Ser Lys Arg Pro Ala Arg Gly Arg Thr Thr Leu Gly Ser Gln
                165                 170                 175

Arg Lys Arg Arg Lys Ser Val Thr Pro Asp Pro Lys Glu Lys Gln Thr
            180                 185                 190

Cys Asp Ile Arg Leu Arg Val Arg Ala Glu Tyr Cys Gln His Glu Thr
        195                 200                 205
```

Ala Leu Gln Gly Asn Val Phe Ser Asn Lys Gln Asp Pro Leu Glu Arg
    210                 215                 220

Gln Phe Glu Arg Phe Asn Gln Ala Asn Thr Ile Leu Lys Ser Arg Asp
225                 230                 235                 240

Leu Gly Ser Ile Ile Cys Asp Ile Lys Phe Ser Glu Leu Thr Tyr Leu
                245                 250                 255

Asp Ala Phe Trp Arg Asp Tyr Ile Asn Gly Ser Leu Leu Glu Ala Leu
                260                 265                 270

Lys Gly Val Phe Ile Thr Asp Ser Leu Lys Gln Ala Val Gly His Glu
            275                 280                 285

Ala Ile Lys Leu Leu Val Asn Val Asp Glu Glu Asp Tyr Glu Leu Gly
        290                 295                 300

Arg Gln Lys Leu Leu Arg Asn Leu Met Leu Gln Ala Leu Pro
305                 310                 315

<210> SEQ ID NO 4
<211> LENGTH: 1142
<212> TYPE: DNA
<213> ORGANISM: Mus musculus

<400> SEQUENCE: 4

```
aaagcactgt atttctgagc ctctagcatg gcgggcctaa agaggcgggc aagccaggtg   60
tggcccgaag agcgtgggga gcaagaacat gggctctaca gcctccaccg catgttcgac  120
atcgtgggca cccacctaac acacagagat gtccgagtgc tttccttcct tttgttgat   180
gttattgatg accatgaacg tggactcatc cgaaatggac gtgacttctt attggcactg  240
gagcgccagg gccgctgtga cgagagtaac tttcgccagg tgctgcagct gctgcgcatc  300
atcactcgcc atgacttgct gccctacgtt actctcaaga gagacgagc tgtgtgccct   360
gatcttgtag acaagtatct ggaggaaaca tcaattcgct atgtgacccc cagagccctc  420
agtgacccag aaccgaggcc tccccagccc tctaaaacag tgcctcccca ctatcctgtg  480
gtgtgctgcc ccacttcggg ttctcaaatg tgtagtaagc ggccagcccg agggagaacc  540
acacttggga gccagcgaaa acgccggaag tcggtgacac cagacccgaa ggaaaagcag  600
acatgtgata tcaggctccg agttcgggcg gaatactgcc agcatgagac ggctctgcaa  660
ggcaatgtct tctccaataa gcaggaccca cttgagcgcc agtttgagcg ctttaaccag  720
gccaacacta tcctcaagtc ccgggacctg ggctccatca tctgtgacat caagttctct  780
gagctcacct acctcgacgc attctggcga gactacatta tggctcatt attagaggca  840
ctgaaaggtg tcttcatcac agactctctc aagcaagctg tgggccatga agccatcaag  900
ctgctggtga acgtggatga ggaggactat gagctgggcc gacagaaact cctgaggaac  960
ttgatgctgc aggcattacc ctgacctttc cccttctcac ctttctgggg actgttcgct 1020
ccgtcacctc tggagctgac atactgttct ggggtttgtt ctctacccct tccaaccaat 1080
cacaccgcct tttttttttt tttttttttt aaaggaaaa gacaaaggaa ggtggaagtg 1140
gt                                                                1142
```

<210> SEQ ID NO 5
<211> LENGTH: 114
<212> TYPE: PRT
<213> ORGANISM: Artificial Sequence
<220> FEATURE:
<223> OTHER INFORMATION: N-DEDD, which is a deletion mutant of human
      DEDD comprising the amino acids 1-114 of the naturally
      occurring human DEDD.

```
<400> SEQUENCE: 5

Met Ala Gly Leu Lys Arg Arg Ala Ser Gln Val Trp Pro Glu His
1               5                   10                  15

Gly Glu Gln Glu His Gly Leu Tyr Ser Leu His Arg Met Phe Asp Ile
            20                  25                  30

Val Gly Thr His Leu Thr His Arg Asp Val Arg Val Leu Ser Phe Leu
        35                  40                  45

Phe Val Asp Val Ile Asp Asp His Glu Arg Gly Leu Ile Arg Asn Gly
    50                  55                  60

Arg Asp Phe Leu Leu Ala Leu Glu Arg Gln Gly Arg Cys Asp Glu Ser
65                  70                  75                  80

Asn Phe Arg Gln Val Leu Gln Leu Leu Arg Ile Ile Thr Arg His Asp
                85                  90                  95

Leu Leu Pro Tyr Val Thr Leu Lys Arg Arg Arg Ala Val Cys Pro Asp
            100                 105                 110

Leu Val

<210> SEQ ID NO 6
<211> LENGTH: 210
<212> TYPE: PRT
<213> ORGANISM: Artificial Sequence
<220> FEATURE:
<223> OTHER INFORMATION: C-DEDD, which is a deletion mutant of human DEDD comprising amino
      acids 109-318 of the naturally occurring humna DEDD.

<400> SEQUENCE: 6

Val Cys Pro Asp Leu Val Asp Lys Tyr Leu Glu Glu Thr Ser Ile Arg
1               5                   10                  15

Tyr Val Thr Pro Arg Ala Leu Ser Asp Pro Glu Pro Arg Pro Pro Gln
            20                  25                  30

Pro Ser Lys Thr Val Pro Pro His Tyr Pro Val Val Cys Cys Pro Thr
            35                  40                  45

Ser Gly Pro Gln Met Cys Ser Lys Arg Pro Ala Arg Gly Arg Ala Thr
    50                  55                  60

Leu Gly Ser Gln Arg Lys Arg Arg Lys Ser Val Thr Pro Asp Pro Lys
65                  70                  75                  80

Glu Lys Gln Thr Cys Asp Ile Arg Leu Arg Val Arg Ala Glu Tyr Cys
                85                  90                  95

Gln His Glu Thr Ala Leu Gln Gly Asn Val Phe Ser Asn Lys Gln Asp
            100                 105                 110

Pro Leu Glu Arg Gln Phe Glu Arg Phe Asn Gln Ala Asn Thr Ile Leu
        115                 120                 125

Lys Ser Arg Asp Leu Gly Ser Ile Ile Cys Asp Ile Lys Phe Ser Glu
130                 135                 140

Leu Thr Tyr Leu Asp Ala Phe Trp Arg Asp Tyr Ile Asn Gly Ser Leu
145                 150                 155                 160

Leu Glu Ala Leu Lys Gly Val Phe Ile Thr Asp Ser Leu Lys Gln Ala
                165                 170                 175

Val Gly His Glu Ala Ile Lys Leu Leu Val Asn Val Asp Glu Glu Asp
            180                 185                 190

Tyr Glu Leu Gly Arg Gln Lys Leu Leu Arg Asn Leu Met Leu Gln Ala
        195                 200                 205

Leu Pro
    210
```

```
<210> SEQ ID NO 7
<211> LENGTH: 342
<212> TYPE: DNA
<213> ORGANISM: Artificial Sequence
<220> FEATURE:
<223> OTHER INFORMATION: Truncated segment of the DNA sequence
      encoding human DEDD, comprising nucleotides 28-369 of
      SEQ ID NO 2.

<400> SEQUENCE: 7
atggcgggcc taaagcggcg ggcaagccag gtgtggccag aagagcatgg tgagcaggaa      60
cacgggctgt acagcctgca ccgcatgttt gacatcgtgg gcactcatct gacacacaga    120
gatgtgcgcg tgctttcttt cctctttgtt gatgtcattg atgaccacga gcgtggactc    180
atccgaaatg gacgtgactt cttattggca ctggagcgcc agggccgctg tgatgaaagt    240
aactttcgcc aggtgctgca gctgctgcgc atcatcactc gccacgacct gctgccctac    300
gtcaccctca gaggagacg ggctgtgtgc cctgatcttg ta                        342

<210> SEQ ID NO 8
<211> LENGTH: 630
<212> TYPE: DNA
<213> ORGANISM: Artificial Sequence
<220> FEATURE:
<223> OTHER INFORMATION: Truncated segment of the DNA sequence
      encoding human DEDD, comprising nucleotides 352-981 of
      SEQ ID NO 2.

<400> SEQUENCE: 8
gtgtgccctg atcttgtaga caagtatctg gaggagacat caattcgcta tgtgacccc      60 agagccctca gtgatccaga accaaggcct ccccagccct ctaaaacagt gcctccccac    120
tatcctgtgg tgtgttgccc cacttcgggt cctcagatgt gtagcaagcg gccagcccga    180
gggagagcca cacttgggag ccagcgaaaa cgccggaagt cagtgacacc agatcccaag    240
gagaagcaga catgtgacat cagactgcgg gttcgggctg aatactgcca gcatgagact    300
gctctgcagg gcaatgtctt ctctaacaag caggacccac ttgagcgcca gtttgagcgc    360
tttaaccagg ccaacaccat cctcaagtcc cgggacctgg gctccatcat ctgtgacatc    420
aagttctctg agctcaccta cctcgatgca ttctggcgtg actacatcaa tggctctta    480 ttagaggcac ttaaaggtgt cttcatcaca gactccctca gcaagctgt gggccatgaa    540 gccatcaagc tgctggtaaa tgtagacgag gaggactatg agctgggccg acagaaactc    600
ctgaggaact tgatgctgca agcattgccc                                     630

<210> SEQ ID NO 9
<211> LENGTH: 35
<212> TYPE: DNA
<213> ORGANISM: Artificial Sequence
<220> FEATURE:
<223> OTHER INFORMATION: Synthetic Construct

<400> SEQUENCE: 9
cgcggatccg ggagcatggc gggcctaaag cggcg                                35

<210> SEQ ID NO 10
<211> LENGTH: 35
<212> TYPE: DNA
<213> ORGANISM: Artificial Sequence
<220> FEATURE:
<223> OTHER INFORMATION: Synthetic Construct
```

```
<400> SEQUENCE: 10
ccggaattcc ggcttggttc tggatcactg aaggc                                    35
```

MUTANT DEDD PROTEINS FOR REGULATING APOPTOSIS

1. CROSS-REFERENCE TO RELATED APPLICATIONS

This application is a continuation-in-part of and claims priority under the provisions 35 U.S.C. §111 of International Patent Application No. PCT/DE99/01712 filed Jun. 8, 1999, which in turn claims priority of German Patent Application No. 198 25 621.3 filed Jun. 8, 1998. The entire disclosure of each of these patent applications is incorporated herein by reference.

2. FIELD OF THE INVENTION

The invention relates to a protein for regulating apoptosis and to a nucleic acid encoding the protein. The protein and nucleic acids are useful in the regulation of apoptosis, and in methods for diagnosing or detecting apoptosis. The invention also relates to antibodies directed against the protein.

3. BACKGROUND OF THE INVENTION

Apoptosis is a type of cell death, which is thought to be genetically programmed, and which is distinct from the process of necrosis. During apoptosis, cells generally se their cell junctions and microvilli, the cytoplasm condenses and nuclear chromatin marginates into a number of discrete masses. Cory, S. *Nature* 367:317–318 (1994).

Apoptosis can be induced via a variety of receptors, commonly referred to as "death receptors." These receptors contain a "death domain" (DD). Examples include CD95, TNF-RI, DR3, DR4 or DR5, which induce apoptosis signal paths after binding their respective ligands. For example, after the CD95 ligand binds to the CD95 receptor, the receptor interacts with the adapter protein FADD/MORTI to induce the recruitment and activation of the protease FLICE/Caspase-8 at the DISC "death inducing signaling complex." FADD and FLICE contain "death effector domains (DED).

Apoptosis can be inhibited by the transcription of anti-apoptotic genes, i.e. by the gene products thereof. For example, the protein FLIP "FLICE-inhibitory protein" inhibits the CD95 apoptosis signal path. German patent 19713434 of Deutsches Krebsforschungszentrum (the German Cancer Research Center). There is a need in the art for novel compounds for regulating of apoptosis, and for methods for using such compounds. It is thus an object of the present invention to provide such compounds and methods.

4. SUMMARY OF THE INVENTION

The invention relates generally to proteins for regulating and/or inducing apoptosis. The proteins of the invention generally include the amino acid sequence of FIG. 1A (SEQ ID NO: 1) or an amino acid sequence which is substantially similar to the amino acid sequence of FIG. 1A (SEQ ID NO: 1). Alternatively, the protein may consist of or consist essentially of the amino acid sequence of FIG. 1A (SEQ ID NO: 1) or an amino acid sequence which is substantially similar to the amino acid sequence of FIG. 1A (SEQ ID NO: 1).

Figure 1C:
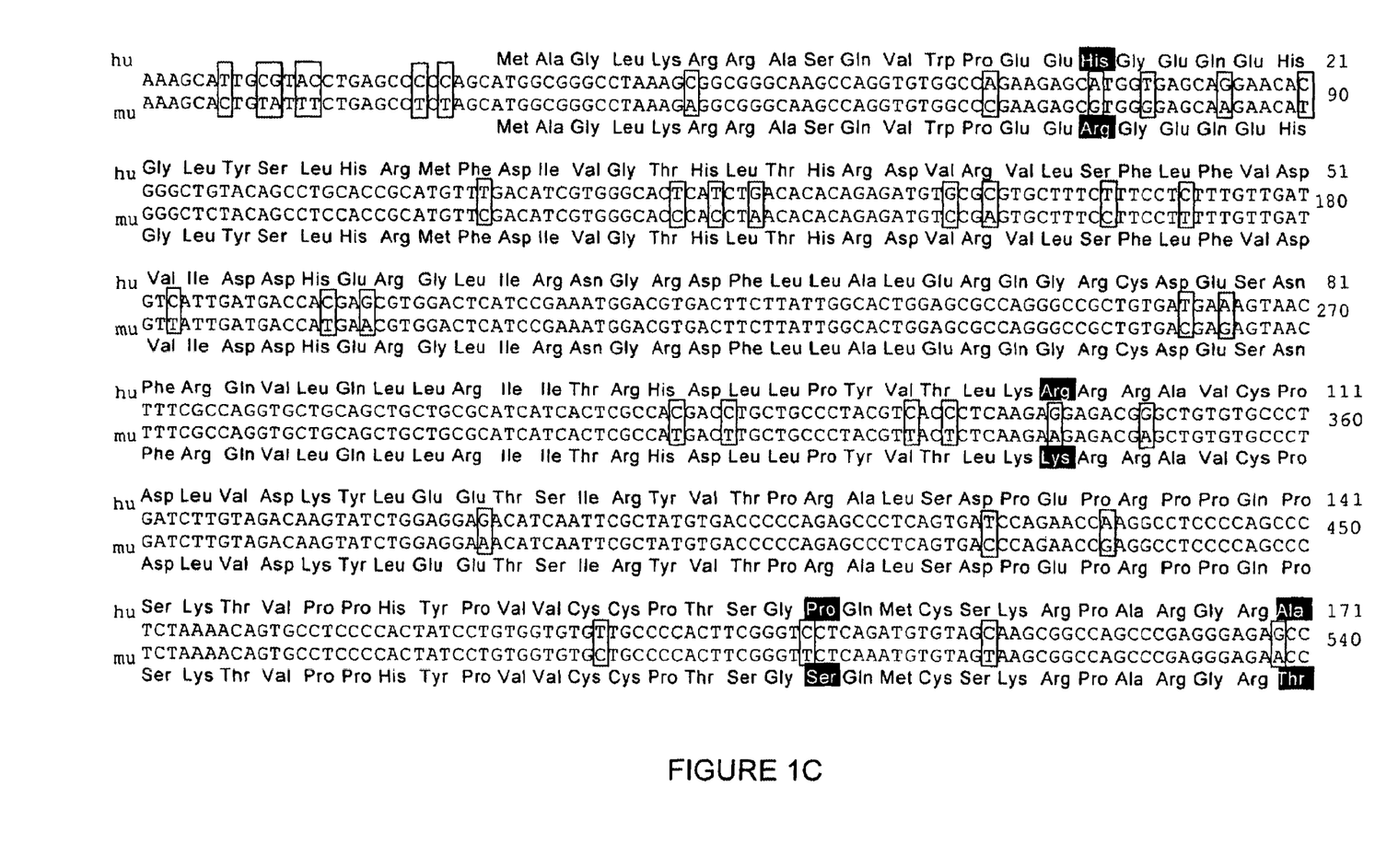
Figure 1D:
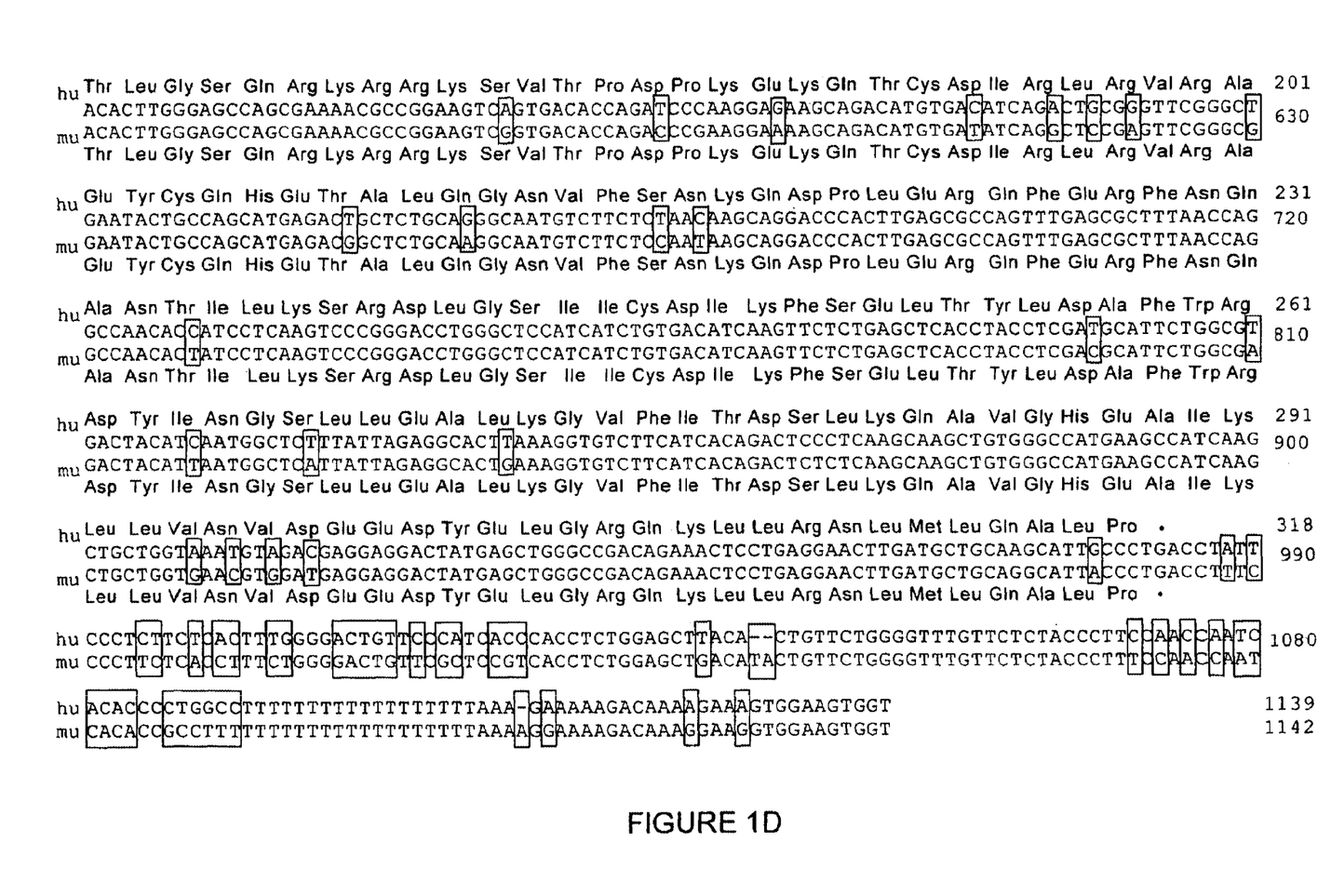
Figure 2:
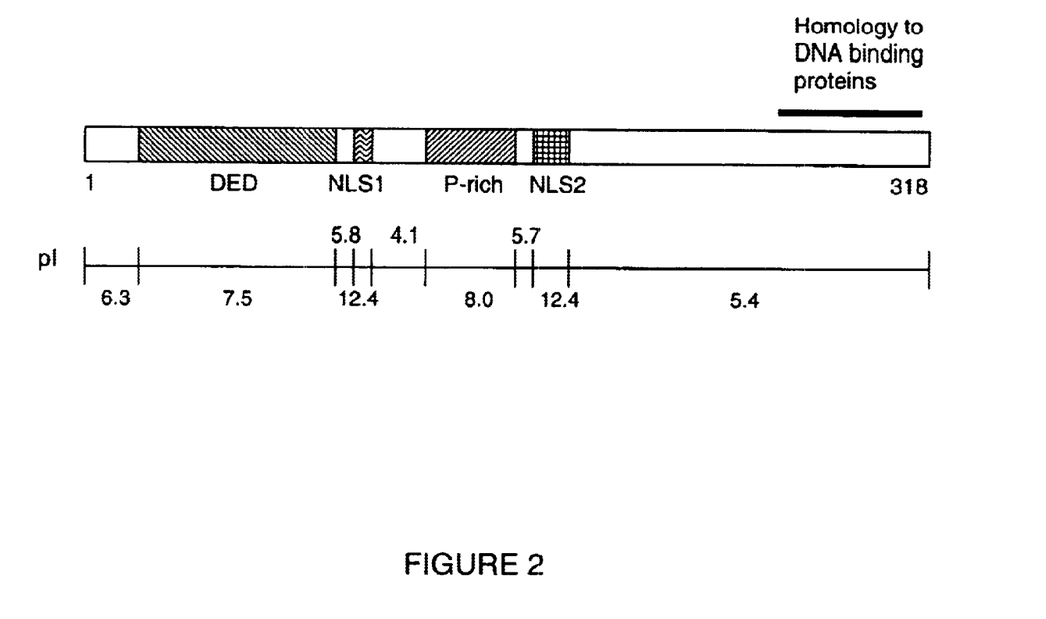
FIG. 2 shows the structural organization of DEDD, DED designating "death effector domain," NLS representing "nuclear localization signal" and P-rich identifying the P-rich region. The isoelectric points for the individual domains are given.
Figure 3:
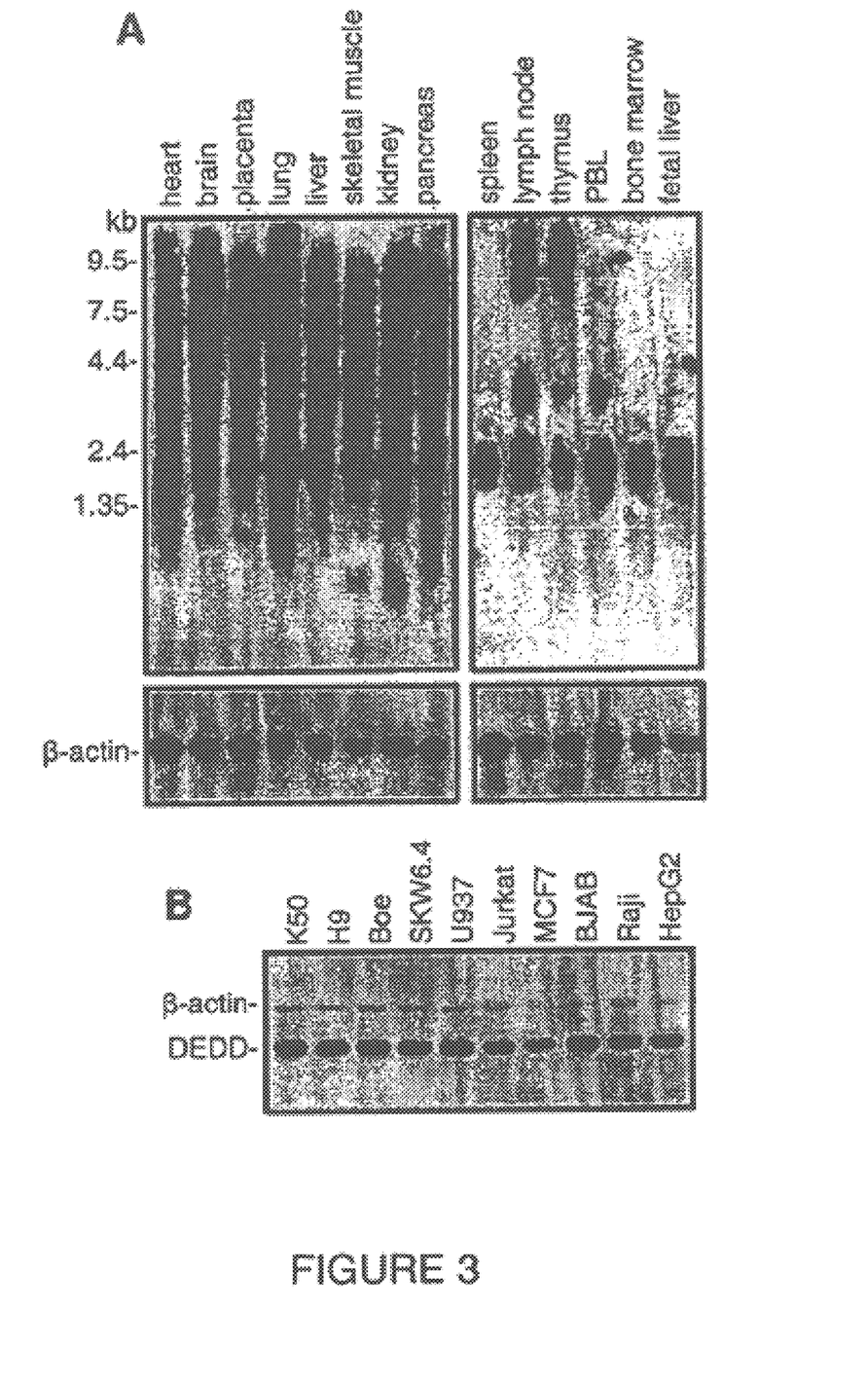
FIG. 3 shows the detection fo DEDD mRNA in tissues (FIG. 3A) or tumor cells (FIG. 3B).
Figure 4:
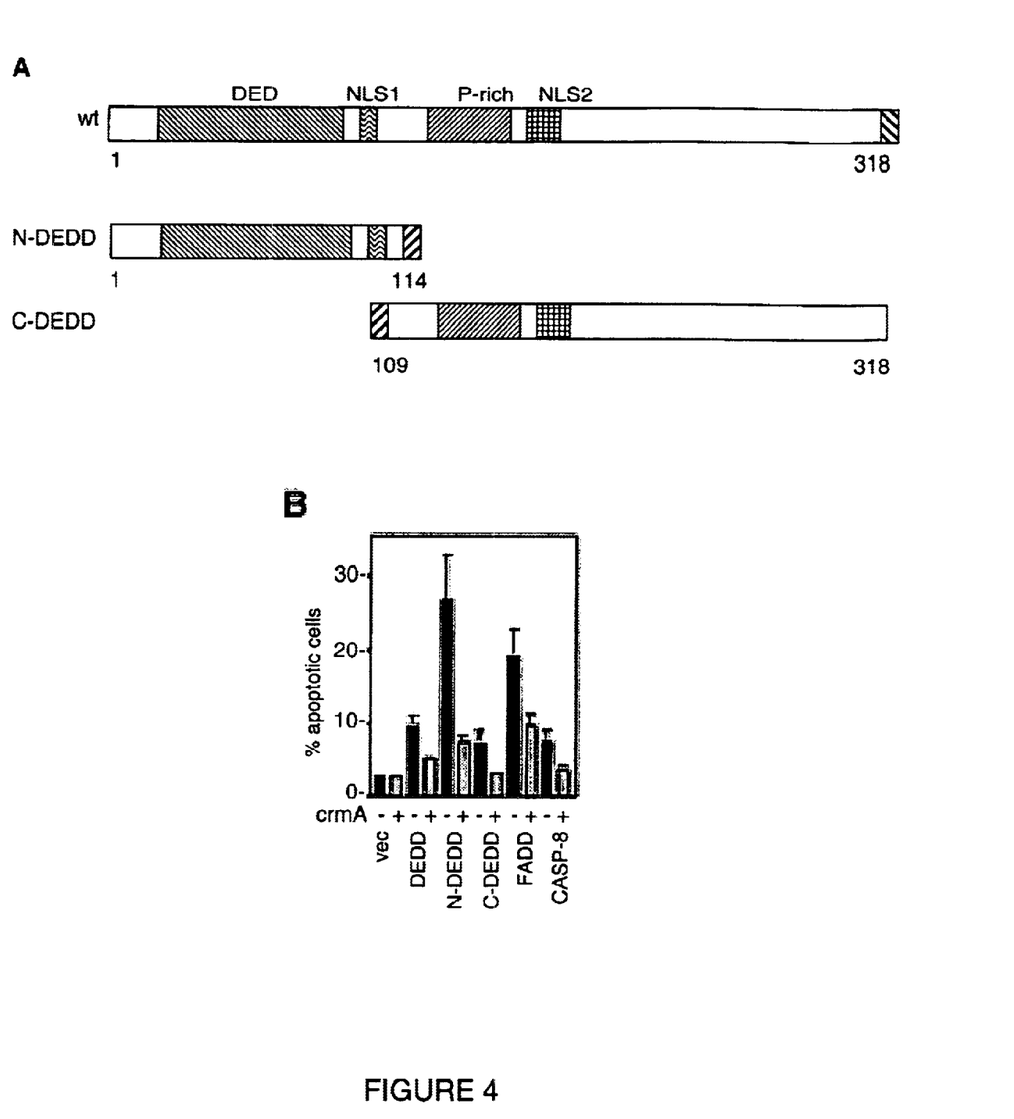
FIG. 4 shows the induction of apoptosis by DEDD.
Figure 5:
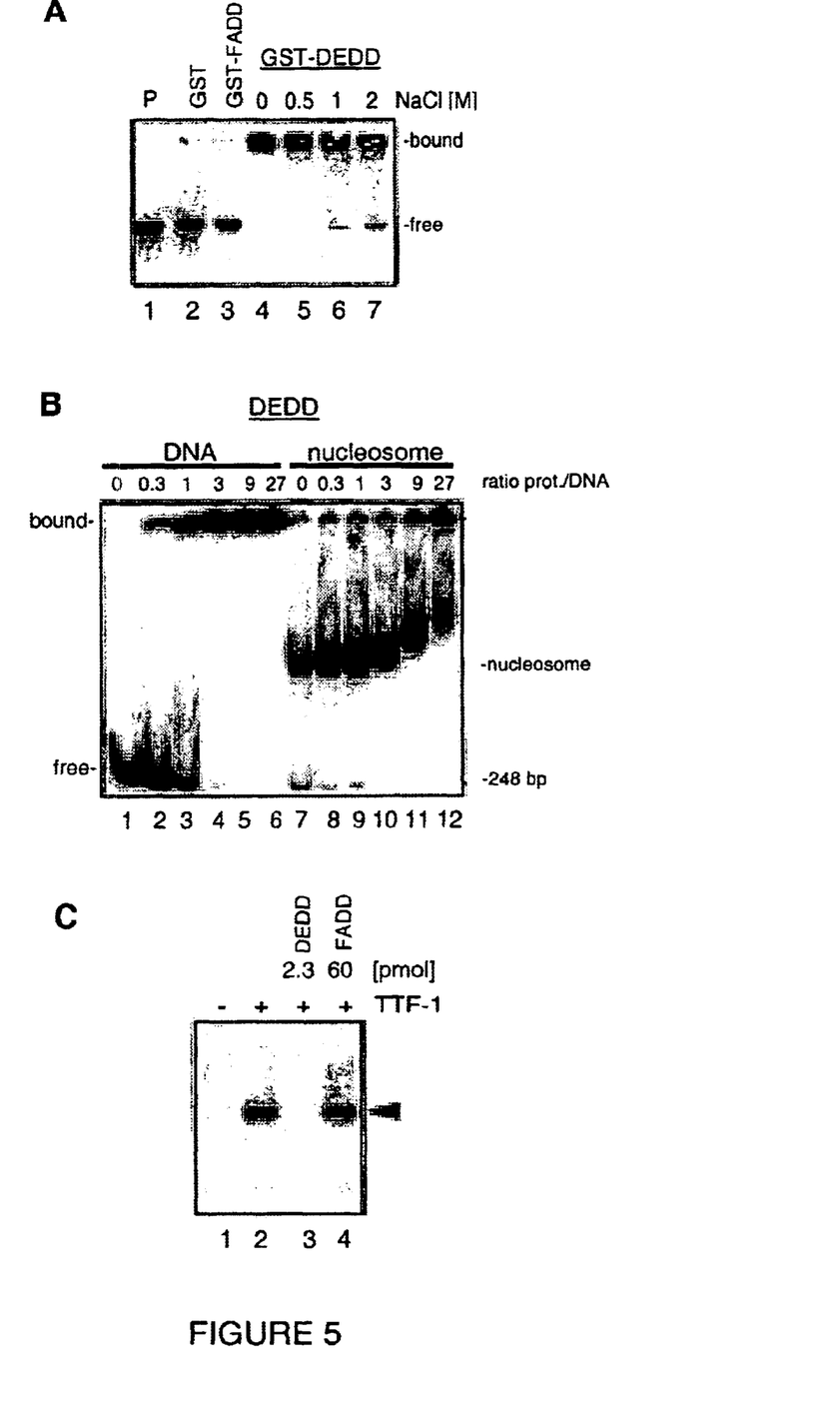
FIG. 5 shows DEDD as a DNA binding protein which in nucleoli inhibits the transcription of ribosomal DNA.

In one aspect the invention relates to an amino acid sequence differing from the amino acid sequence of FIG. 1A (SEQ ID NO: 1) by one or more amino acids, wherein the DNA encoding the amino acid sequence hybridizes with the DNA encoding the amino acid sequence of FIG. 1A (SEQ ID NO: 1). Preferably, the amino acid sequence differs from the amino acid sequence of FIG. 1A (SEQ ID NO: 1) by no more than 1, 2, 3, 4, or 5 amino acids. The amino acid sequence may also be an active fragment of the sequence of FIG. 1A (SEQ ID NO: 1) or of an amino acid sequence which is substantially similar to an active fragment. Examples of active fragments include amino acids 1–114 of FIG. 1A (SEQ ID NO: 1) or amino acids 109–318 of FIG. 1A (SEQ ID NO: 1). Additionally, the amino acid sequence may be a truncation of the amino acid sequence of FIG. 1A (SEQ ID NO: 1), i.e., truncated at the C-terminus and/or the N-terminus, preferably by no more than 1, 2, 3, 4, or 5 amino acids at either terminus. The amino acid sequence may also comprise one or more conservative substitutions.

In a related aspect, the amino acid sequence differs from the amino acid sequence of FIG. 1A (SEQ ID NO: 1) by one or more amino acids and hybridizes to the DNA encoding the amino acid sequence of FIG. 1A (SEQ ID NO: 1), preferably under stringent conditions.

The protein of the invention is suitably provided as a component of a pharmaceutical composition.

The invention also relates to a nucleic acid, such as a DNA or RNA encoding any of the proteins of the invention. In one aspect, the DNA comprises the nucleotide sequence of FIG. 1A (SEQ ID NO: 2) or a nucleotide sequence which is substantially similar to the nucleotide sequence of FIG. 1A (SEQ ID NO: 2). The DNA may differ from the DNA of FIG. 1A (SEQ ID NO: 2) by one or more degenerate codons. In a preferred aspect, the DNA comprises a nucleotide sequence corresponding to, or substantially similar to, nucleotides 28 to 369 of FIG. 1A (SEQ ID NO: 2), as provided in SEQ ID NO: 7, nucleotides 352 to 981 of FIG. 1A (SEQ ID NO: 2), as provided in SEQ ID NO: 8, or the nucleotide sequence of FIG. 1B (SEQ ID NO: 4). The nucleotide sequence is suitably provided as a component of an expression plasmid or an expression cassette, or as a component of a cell transformed by a nucleic acid comprising the nucleotide sequence.

The invention also relates to a process for preparing a protein of the invention. In one aspect, the method of production comprises culturing a cell transformed by an expression plasmid comprising a nucleotide sequence selected from the following: (a) the nucleotide sequence of FIG. 1A (SEQ ID NO: 2); (b) a nucleotide sequence which is substantially similar to the nucleotide sequence of FIG. 1A (SEQ ID NO: 2); (c) a nucleotide sequence which is substantially similar to the nucleotide sequence of FIG. 1A (SEQ ID NO: 2); (d) a nucleotide sequence which hybridizes to the nucleotide sequence of FIG. 1A (SEQ ID NO: 2), preferably under stringent conditions; (e) a nucleotide sequence which differs from the nucleotide sequence of FIG. 1A (SEQ ID NO: 2) by one or more degenerate codons; (f) a nucleotide sequence corresponding to nucleotides 28 to 369 of FIG. 1A (SEQ ID NO: 2), as provided in SEQ ID NO: 7, or a nucleotide sequence substantially similar thereto; (g) a nucleotide sequence corresponding to nucleotides 352 to 981 of FIG. 1A (SEQ ID NO: 2), as provided in SEQ ID NO: 8; and (h) the nucleotide sequence of FIG. 1B (SEQ ID NO: 4) or a nucleotide sequence substantially similar thereto.

In another aspect, the invention provides an antibody which binds, preferably which specifically binds, to a protein of the invention. The antibody is preferably a monoclonal antibody. In a related aspect, the invention relates to a hybridoma cell line expressing an antibody of the invention.

The invention also relates to a method for detecting in a sample the presence a protein of the invention. In general, the method employs the following steps: (a) contacting the sample with a an antibody which specifically binds to a target protein of the invention; and (b) analyzing the sample for the presence of antibody specifically bound to target protein.

Similarly, the invention relates to a method for islolating a protein of the invention. The method generally employs the following steps: (a) contacting a composition comprising the target protein with an antibody which specifically binds to the target protein; (b) eluting the target protein from the antibody. The eluted protein may then be separated using known procedures, for example, standard cross-flow filtration techniques known in the art.

In another aspect, the invention relates to a method for inducing apoptosis in a cell. In this method, apoptosis is induced by contacting the cell with a protein of the invention. The cell may be contacted in vivo by administration of the protein of the invention to a subject in an amount sufficient to induce apoptosis. The method is useful, for example, in the treatment of diseases of the immune system and in the treatment of neoplasms. The administration may be direct, by administering the protein to the subject, or indirect, by administering to the subject a nucleotide encoding the protein for expression in the subject.

5. DEFINITIONS

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "identical" or "identity" in the context of two nucleic acids or polypeptide sequences refers to the residues in the two sequences which are the same when aligned for maximum correspondence. Optimal alignment of sequences for comparison can be conducted, e.g., by the local homology algorithm of Smith and Waterman Adv. Appl. Math. 2: 482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The term "substantial identity" or "substantial similarity" in the context of a polypeptide indicates that a polypeptide comprises a sequence with at least 70% sequence identity to a reference sequence, or preferably 80%, or more preferably 85% sequence identity to the reference sequence, or most preferably 90% identity over a comparison window of about 10–20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

An indication that two nucleotide sequences are substantially identical is that the polypeptide which the first nucleic acid encodes is immunologically cross reactive with the polypeptide encoded by the second nucleic acid.

Another indication that two nucleotide sequences are substantially identical is that the two molecules hybridize to each other under stringent conditions. Stringent conditions are sequence dependent and are different under different environmental parameters. Generally, stringent conditions are selected to be about 5° C. to 20° C. lower than the thermal melting point (T[m]) for the specific sequence at a defined ionic strength and pH. The T[m] is the temperature (under defined ionic strength and pH) at which 50% of the target sequence hybridizes to a perfectly matched probe. However, nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The phrases "specifically binds to a protein" or "specifically hybridizes to" or "specifically immunoreactive with," refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, N.Y., for a description of immunoassay formats and conditions that can be used to determine specific immunoreactivity.

The terms "isolated," "purified," or "biologically pure" refer to material which is substantially or essentially free from components which normally accompany it as found in its native state.

The term "antibody" as used herein, includes various forms of modified or altered antibodies, such as an intact immunoglobulin, various fragments such as an Fv fragment, an Fv fragment containing only the light and heavy chain variable regions, an Fv fragment linked by a disulfide bond (Brinkmann, et al. Proc. Natl. Acad. Sci. USA, 90: 547–551 (1993)), a Fab or (Fab)'2 fragment containing the variable regions and parts of the constant regions, a single-chain antibody and the like (Bird et al., Science 242: 424–426 (1988); Huston et al., Proc. Nat. Acad. Sci. USA 85: 5879–5883 (1988)). The antibody may be of animal (especially mouse or rat) or human origin or may be chimeric (Morrison et al., Proc Nat. Acad. Sci. USA 81: 6851–6855 (1984)) or humanized (Jones et al., Nature 321: 522–525 (1986), and published UK patent application #8707252).

The terms "peptide," "polypeptide" and "protein" are used interchangeably herein to refer to an amino acid chain with two or more amino acid residues, and also includes branched and circularized amino acid chains.

BRIEF DESCRIPTION OF THE DRAWINGS

FIG. 1 shows the DNA and amino acid sequence of a protein of the invention (DEDD) from humans (FIG. 1A (SEQ ID NO: 1 and 2)) and mice (FIG. 1B (SEQ ID NO: 3 and 4) and the differences between the human and mouse sequences (FIG. 1C and FIG. 1D).

FIG. 4A shows deletion mutants of DEDD, N-DEDD (SEQ ID NO: 5) and C-DEDD (SEQ ID NO: 6), and FIG. 4B shows apoptosis induced by DEDD or these deletion mutants.

FIG. 5A shows the binding of GST-DEDD λ-DNA. FIG. 5B shows the binding of GST-DEDD to DNA assembled to a nucleosome. FIG. 5C shows that the transcription of an rDNA minigene, which requires the RNA polymerase I-termination factor (TTF-I), is inhibited by GST-DEDD.

6. DETAILED DESCRIPTION OF THE INVENTION

The present invention is based on the inventors' surprising discovery of a protein, referred to herein as DEDD, which is useful in the regulation, and particularly in the induction of apoptosis. In addition to the amino acid sequence, which is set forth in FIG. 1A (SEQ ID NO: 1), the inventors have characterized DEDD by a number of relevant physical and chemical attributes: size of about 34 kD; N-terminal "death effector domain" (DED); C-terminal regions having homologies to DNA binding proteins, such as histones; capacity to form a strong complex with DNA; and ubiquitous expression. Moreover, following the induction of the CD95 apoptosis signal path, the protein migrates by means of two nuclear localization signals (NLS) into the nucleus or nucleoli where it inhibits the transcription of ribosomal DNA (FIGS. 2–5), thereby inhibiting protein biosynthesis, including biosynthesis of gene products of anti-apoptotic genes.

The proteins of the invention are useful for regulating apoptosis. In a preferred aspect, the protein comprises the amino acid sequence of DEDD (SEQ ID NO: 1) or a substantially similar amino acid sequence (as defined herein), e.g., a sequence differing from the sequence of FIG. 1A (SEQ ID NO: 1) by one or several amino acids. In a preferred aspect, the protein comprises any amino acid sequence coding for DEDD with a nucleotide sequence which hybridizes with the DNA of FIG. 1A (SEQ ID NO: 2). The sequence may, for example, differ from the DNA of FIG. 1A (SEQ ID NO: 2) by additions, deletions, substitutions and/or inversions of one or several base pairs. For example, the DNA sequence can be that of FIG. 1B (SEQ ID NO: 4). The DNA sequence can also be one coding for N-DEDD (SEQ ID NO: 5) or C-DEDD (SEQ ID NO: 6) (Example 2 and FIG. 4A). In a preferred embodiment, the invention provides a protein which hybridizes to any of the nucleotide sequences of DEDD (SEQ ID NO: 2), N-DEDD (SEQ ID NO: 5) or C-DEDD (SEQ ID NO: 6) under common conditions, in particular at 20° C. below the melting point of the sequence.

The invention also provides a nucleic acid encoding DEDD (SEQ ID NO: 2). The nucleic acid may be an RNA or a DNA, e.g. a cDNA. In a preferred aspect of the invention, the DNA is as shown in FIG. 1A (SEQ ID NO: 2) or is substantially similar to the DNA shown in FIG. 1A (SEQ ID NO: 2). In a preferred aspect, the DNA differs from the DNA shown in FIG. 1A (SEQ ID NO: 2) by one or several base pairs and hybridizes with the DNA of FIG. 1A (SEQ ID NO: 2), preferably under common conditions, more preferably under stringent conditions. A DNA differing from the DNA shown in FIG. 1A (SEQ ID NO: 2) by one or more degenerate codons is also within the scope of the invention.

The DNA of the invention may differ from the DNA of FIG. 1A (SEQ ID NO: 2) by additions, deletions, substitutions and/or inversions of one or several base pairs, so long as the DNA is substantially similar to the DNA shown in FIG. 1A (SEQ ID NO: 2). A preferred DNA sequence is shown in FIG. 1B (SEQ ID NO: 4) or a substantially similar sequence. Preferred DNA sequences are those which encode N-DEDD (SEQ ID NO: 5) or C-DEDD (SEQ ID NO: 6) (Example 2 and FIG. 4A).

The DNAs of FIGS. 1A and B (SEQ ID NOS: 2 and 4) were deposited as plasmid with the DSMZ (Deutsche Sammlung von Mikroorganismen und Zellen) [German-type collection of micro-organisms and cells] under DSM 12174 on May 14, 1998 under the provisions of the Budapest Treaty.

A DNA of the invention may be provided alone (i.e., without flanking sequences) or as a component of a larger sequence comprising other sequences. For example, a DNA of the invention is suitably provided as a component of an expression cassette or an expression vector. Many examples of expression cassettes, expression vectors and the like are known in the art. Examples of expression vectors for expression in E. coli include pGEMEX, pUC derivatives, pGEX-2T, pET3b and pQE-8. Examples of expression vectors for expression in yeast include pY100 and Ycpad1. Examples of expression vectors for expression in animal cells include pKCR, pEFBOS, cDM8 and pCEV4. A suitable expression vector for expression in insect cells is the bacculovirus expression vector pAcSGHisNT-A.

Many cell lines and other organisms useful in the expression of proteins are known in the art. Examples of cell lines include the E. coli strains HB101, DH1, x1776, JM101, JM 109, BL21 and SG 13009; the yeast strain Saccharomyces cerevisiae; the animal cell lines L, NIH 3T3, FM3A, CHO, COS, Vero and HeLa; and the sf9 insect cell line.

Methods for transforming or transfecting cells for the expression of an expression vector are known in the art. The DNA of the invention can also be ligated to a DNA encoding another protein and/or peptide, so that the DNA of the invention is expressed as a component of a fusion protein.

Conditions for culturing transformed or transfected cells are also known in the art, as are methods for isolating and purifying the expressed protein and/or fusion protein.

The invention also provides antibodies directed against a protein or fusion protein of the invention. The production of such antibodies may proceed according to known methods using the novel proteins of the invention. Antibodies of the invention may be polyclonal or monoclonal. Production of antibodies may be accomplished by immunizing an animal, such as a rabbit or chicken (for a polyclonal antibody) or a mouse (for a monoclonal antibody), with a protein, fusion protein, or protein fragment of the invention. Further "boosters" of the animals can be effected with the same protein, fusion or with fragments. A polyclonal antibody can be obtained, for example, from the animal serum or egg yolk. To obtain a monoclonal antibody, animal spleen cells are fused with myeloma cells using standard protocols.

The invention also provides a kit comprising one or several of the following components: a DNA of the invention, a protein of the invention (DEDD), an antibody of the invention, and conventional auxiliary agents, such as carriers, buffers, solvents, controls, etc. One or several embodiments may be included.

The proteins of the invention are useful for inducing apoptosis. Moreover, the proteins and antibodies are useful in the investigation of apoptosis. A relationship, in particular as to time and quantity, between DEDD and apoptosis, in particular its regulation, can be established. In addition, an autoantibody directed against the protein can be detected in an assay using DEDD. These analyses can be accomplished using known methods, such as Western blot, ELISA, immunoprecipitation and immunofluorescence. Furthermore, the organization and expression of the gene coding for DEDD can be detected with a nucleic acid of the invention, in particular a DNA and primers derived therefrom. This analysis can be accomplished using standard procedures, such as Southern blot and via "in situ" hybridization.

The identification of DEDD (SEQ ID NO:1) forms the basis for anti-DEDD therapy in a subject animal, such as a human. For example, the antibodies of the invention are useful in the inhibition of DEDD in animals. Moreover, DEDD can be used in high throughput screening assays to identify other compounds which inhibit the activity of DEDD. Antisense therapy can also be used to prevent translation of DEDD in a subject.

On the other hand, DEDD and substantially similar proteins can be used to induce therapeutic apoptosis in an animal subject, such as a human subject. DEDD and substantially similar proteins can be administered directly. Various formulations and conjugation techniques are knwn in the art for facilitating administration of polypeptides via oral, parenteral and other routes. Moreover, DEDD and substantially similar proteins can be administered indirectly by administering a nucleic acid encoding such proteins, preferably a DNA controlled by a constitutive or inducible promoter to effect expression of DEDD in vivo. The proteins and/or nucleic acid therapeutics of the invention may be suitably administered using standard formulations known in the art. Examples of conditions treatable according to the methods of the invention include diseases of the immune system (such as AIDS), diseases of the liver and tumoral diseases.

7. EXAMPLES

The invention is illustrated by the following, non-limiting, examples:

7.1 Detection of DEDD mRNA in Tissues or Cells

PolyA RNA from tissues, such as heart, brain, placenta, lung, liver, skeletal muscle, kidney, pancreas, spleen, lymph nodes, thymus, bone marrow and fetal lung, is subjected to a Northern blot hybridization. For this purpose, a membrane containing the polyA RNA (MTN™ Clontech) is used and hybridized with a $^{32}$p-labeled DNA sample of DEDD which codes for DED, the first NLS and parts of the proline-rich region. The hybridization is carried out under the conditions indicated by Clontech (cf. FIG. 3A).

Furthermore, whole RNA is isolated from various lymphoid and non-lymphoid tumor cells and subjected to an RT-PCR, the RT-PCR kit of Perkin Elmer being used under the indicated conditions. The RT-PCR samples are used in a competitive PCR (1 min 95° C., 1 min 59° C., 1 min 72° C., 35 cycles), the primers 3 (5'-CGCGGATCCGGGAGCAT GGCGGGCCTAAAGCGGCG-3') (SEQ ID NO: 9) and 4 (5'-CCGGAATTCCGGCTTGGTTCTGGATCACTGAA GGC-3') (SEQ ID NO: 10) and β-actin primer being used (cf. FIG. 3B).

The results demonstrate that DEDD is expressed ubiquitously.

7.2 Induction of Apoptosis by DEDD or Deletion Mutants Thereof

Two DEDD deletion mutants are produced. One (referred to as N-DEDD) comprises the amino acid 1–114 of DEDD of FIG. 1A (SEQ ID NO: 1), i.e. it comprises DED and NLS1. The other (hereinafter referred to as C-DEDD) comprises the amino acids 109–318 of DEDD of FIG. 1A (SEQ ID NO: 1), i.e. it comprises the proline-rich region, NLS2 and the C-terminal half of DEDD. Furthermore, the DEDD deletion mutants each have a FLAG peptide, namely N-DEDD at the C-terminus and C-DEDD at the N-terminus (FIG. 4A).

293 cells are transiently transfected with DNAs which code for DEDD, N-DEDD and/or C-DEDD. Furthermore, DNAs which code for FADD or Caspase-8 are used as a control. Transfection is carried out by means of the calcium phosphate precipitation method. 36 hours after the transfection the cells are collected and the DNA fragmentation is determined as an indication of apoptosis.

The results demonstrate that DEDD, N-DEDD and C-DEDD can induce apoptosis, the induction effect of N-DEDD being the strongest. Apoptosis induction can be inhibited by co-expression of the serpin caspase inhibitor crmA.

7.3 DNA Binding by DEDD and Inhibition of the Transcription of Ribosomal (r)DNA

DEDD is produced in the form of a glutathione S transferase (GST) DEDD fusion protein. GST-DEDD is used with λ-DNA at 0.5–2M NaCl in a binding test and then subjected to an agarose gel electrophoresis. The same is carried out with GST alone or with GST-FADD (FIG. 5A).

It shows that DEDD may form a complex with a DNA (FIG. 5A, lane 5). This complex is resistant to salt (FIG. 5A, lane 7).

Furthermore, GST-DEDD is used in a binding test with a 248 bp fragment of the mouse rDNA promoter which is assembled into a nucleosome. The molar ratios of GST-DEDD to DNA are 0–27. After the binding test, the reaction batch is subjected to a 4.5% polyacrylamide gel electrophoresis (FIG. 5B).

The results are consistent with a conclusion that DEDD forms a complex with nucleosomes.

In addition, GST-DEDD or GST-FADD are used in an in vitro transcription test. In this test, a mouse rDNA minigene is transcribed in the presence or absence of the RNA polymerase I termination factor (TTF-I). Resulting $^{32}$P-labeled transcripts are subjected to a 4.5% polyacrylamide gel electrophoresis (FIG. 5C).

The results demonstrate that DEDD can inhibit the transcription of rDNA, confirming that DEDD can inhibit the protein biosynthesis and thus the synthesis of gene products of anti-apoptotic genes.

7.4 Production and Purification of a Protein of the Invention (DEDD)

The DNA of FIG. 1A (SEQ ID NO: 2) is provided with BamHI linkers, subsequently cleaved by BamHI and inserted in the BamHI-cleaved expression vector pQE-8 (Qiagen company). The expression plasmid pQE-8/DEDD is obtained. Such a plasmid codes for a fusion protein from 6 histidine residues (N-terminus partner) and the DEDD of the invention of FIG. 1A (SEQ ID NO: 1) (C-terminus partner). pQE-8/DEDD is used for the transformation of *E. coli* SG 13009 (cf. Gottesman, S. et al., J. Bacteriol. 148, (1981), 265–273). The bacteria are cultured in an LB broth with 100 μg/ml ampicillin and 25 μg/ml kanamycin and induced for 4 h with 60 μM isopropyl-β-D-thiogalactopyranoside (IPTG). Lysis of the bacteria is achieved by the addition of 6 M guanidine hydrochloride. Thereafter, chromatography (Ni-NTA resin) is carried out with the lysate in the presence of 8 M urea in accordance with the instructions from the manufacturer (Qiagen) of the chromatography materials. The bound fusion protein is eluted in a buffer having pH 3.5. After its neutralization the fusion protein is subjected to 18% SDS polyacrylamide gel electrophoresis and stained with coomassie blue (Thomas, J. O. and Kornberg, R. D., J. Mol. Biol. 149(1975), 709–733).

The results show that a (fusion) protein of the invention can be produced in highly pure form.

7.5 Production and Detection of an Antibody of the Invention

A fusion protein produced as described in Section 7.4 is subjected to 18% SDS polyacrylamide gel electrophoresis. After staining the gel using 4 M sodium acetate, an about 34 kD band is excised from the gel and incubated in phosphate-buffered common salt solution. Gel pieces are sedimented before the protein concentration of the supernatant is determined by SDS polyacrylamide gel electrophoresis which is followed by coomassie blue staining. Animals are immunized as follows with the purified fusion protein:

7.5.1 Immunization Protocol for Polyclonal Antibodies in Rabbits

35 μg of gel-purified fusion protein in 0.7 ml PBS and 0.7 ml of complete Freund's adjuvant or incomplete Freund's adjuvant are used per immunization:

| Day 0: | 1st immunization (complete Freund's adjuvant) |
| --- | --- |
| Day 14: | 2nd immunization (incomplete Freund's adjuvant' icFA) |
| Day 28: | 3rd immunization (icFA) |
| Day 56: | 4th immunization (icFA) |
| Day 80: | bleeding to death. |

The rabbit serum is tested in an immunoblot. For this purpose, a fusion protein of the invention is subjected to SDS polyacrylamide gel electrophoresis and transferred to a nitrocellulose filter (cf. Khyse-Anderson, J., J. Biochem. Biophys. Meth. 10 (1984), 203–209). The Western blot analysis is carried out as described in Bock, C. -T. et al., Virus Genes 8, (1994), 215–229. For this purpose, the nitrocellulose filter is incubated with a first antibody at 37° C. for one hour. This antibody is the rabbit serum (1:10000 in PBS). After several wash steps using PBS, the nitrocellulose filter is incubated with a second antibody. This antibody is an alkaline phosphatase-coupled monoclonal goat anti-rabbit IgG antibody (Dianova company) (1:5000) in PBS. 30 minutes of incubation at 37° C. are followed by several wash steps using PBS and subsequently by the alkaline phosphatase detection reaction with developer solution (36 μM 5'-bromo-4-chloro-3-indolylphosphate, 400 μM nitro blue tetrazolium, 100 mM Tris-HCl, pH 9.5, 100 mM NaCl, 5 mM $MgCl_2$) at room temperature until bands are visible.

7.5.2 Immunization Protocol for Polyclonal Antibodies in Chickens

40 μg of gel-purified fusion protein in 0.8 ml PBS and 0.8 ml of complete Freund's adjuvant or incomplete Freund's adjuvant are used per immunization.

| Day 0: | 1st immunization (complete Freund's adjuvant) |
| --- | --- |
| Day 28: | 2nd immunization (incomplete Freund's adjuvant; icFA) |
| Day 50: | 3rd immunization (icFA) |

Antibodies are extracted from egg yolk and tested in a Western blot. Polyclonal antibodies of the invention are detected.

7.5.3 Immunization Protocol for Monoclonal Antibodies in Mice

12 μg of gel-purified fusion protein in 0.25 ml PBS and 0.25 ml of complete Freund's adjuvant or incomplete Freund's adjuvant area used per immunization. The fusion protein is dissolved in 0.5 ml (without adjuvant) in the 4th immunization.

| Day 0: | 1st immunization (complete Freund's adjuvant) |
| --- | --- |
| Day 28: | 2nd immunization (imcomplete Freund's adjuvant; icFA) |
| Day 56: | 3rd immunization (icFA) |
| Day 84: | 4th immunization (PBS) |
| Day 87: | fusion. |

Supernatants of hybridomas are tested in a Western blot. Monoclonal antibodies of the invention are detected.

We claim:

1. An isolated protein consisting of SEQ ID NO: 5 or SEQ ID NO: 6.

2. An isolated protein consisting of SEQ ID NO: 5 linked to a FLAG peptide or SEQ ID NO: 6 linked to a FLAG peptide.

3. A composition comprising:

a protein of claim 1; and a pharmaceutically acceptable carrier.

* * * * *